United States Patent
Buchwald et al.

[11] Patent Number: 6,037,181
[45] Date of Patent: Mar. 14, 2000

[54] METHOD AND APPARATUS FOR DETERMINING BLOOD OXYGEN TRANSPORT

[76] Inventors: Henry Buchwald, 6808 Margaret's La., Edina, Minn. 55439; Hector J. Menchaca, 401 S. First St. #1408, Minneapolis, Minn. 55401; Van Michalek, 2839 Aglen Ave. North, Roseville, Minn. 55113; Thomas J. O'Dea, 925 Arbogast St., Shoreview, Minn. 55120; Thomas D. Rohde, 702 Third Ave. SE., Minneapolis, Minn. 55414

[21] Appl. No.: 09/005,474

[22] Filed: Jan. 12, 1998

[51] Int. Cl.⁷ .......................... G01N 33/50; G01N 33/92
[52] U.S. Cl. ................... 436/71; 436/63; 436/68; 436/136; 436/138; 436/181; 422/68.1; 422/83; 422/88; 435/2
[58] Field of Search .................... 436/63, 66, 68, 436/71, 127, 136, 138, 164, 167, 168, 172, 181; 422/68.1, 73, 82.05, 82.08, 83, 88, 99; 435/2

[56] References Cited

U.S. PATENT DOCUMENTS

| | | | |
|---|---|---|---|
| 4,013,417 | 3/1977 | Raffaele | 422/67 |
| 4,133,874 | 1/1979 | Miller et al. | 424/450 |
| 4,209,300 | 6/1980 | Thibault | 436/66 |
| 5,686,300 | 11/1997 | Berndt | 435/287.5 |

FOREIGN PATENT DOCUMENTS

| | | |
|---|---|---|
| 2073485 | 2/1997 | Russian Federation . |
| 1739295 | 6/1992 | U.S.S.R. . |

OTHER PUBLICATIONS

Anderson, H.V. et al., "Coronary artery flow monitoring following coronary interventions," *European Heart Journal*, (Supplement J) 16:71–73 (1995).

Clark, Jr., A. et al. "Oxygen Delivery From Red Cells," *Biophysical Journal*, 47:171–181 (Feb. 1985).

Di Mario, C. et al., "Principles of interpretaion of coronary velocity and pressure tracings", *European Heart Journal*, (Supplement J), 16:53–59 (1995).

Guyton, A.C., *Textbook of Medical Physiology* —eighth edition; sections on coronary blood flow; diffusion; oxygen capacity of blood, pp. 186, 237, 43–44; 434–439 (WB Saunders, Philadelphia, Pa. 1991).

Huxley, V. H., et al., "Effect of Diffusion Boundary Layers on the Initial Uptake of $O_2$ by Red Cells. Theory versus Experiment," *Microvascular Research*, 26:89–107 (1983).

Mendelson, Y. et al., "In–vitro Evaluation of a Dual Oxygen Saturation/Hematocrit Intravascular Fiberoptic Catheter," *Biomedical Instrumentation & Technology*, 24:199–206 (May/Jun. 1990).

Page, T.C. et al., "Chapter 9—Experimental Simulation of Oxygen Transport in Microvessels," pp. 132–145 (undated).

Page, T.C. et al., "Oxygen Transport by Erythroctye/Hemoglobin Solution Mixtures in an in Vitro Capillary as a Model of Hemoglobin—Based Oxygen Carrier Performance," *Microvascular Research*, 55:54–64 (1998).

Popel, A.S., "Theory of Oxygen Transport to Tissue," *Critical Reviews in Biomedical Engineering*, 17(3):257–321 (1989).

Steinbach, J.H. et al., "High Blood Cholesterol Reduces in Vitro Blood Oxygen Delivery," *Journal of Surgical Research*, 16:134–139 (1974).

Tsai, A. G. et al., "Chapter 8 —Microvascular Oxygen Distribution: Effects Due to Free Hemoglobin in Plasma," pp. 124–131 (undated).

Villars, F.M. et al., *Physics with Illustrative Examples from Medicine and Biology*, vol. 2. Statistical Physics; sections on the diffusion equation; Particle Conversation and Fick's Law; Transport of Water and Solute Across Biological Membranes, pp. 2–46 to 2–47; 2–66 to 2–79; 2–81 to 2–83; 2–92 to 2–97; 2–106; 2–192 to 2–203 (Addison–Wesley, Reading, Mass., 1974).

*Primary Examiner*—Maureen M. Wallenhorst
*Attorney, Agent, or Firm*—Merchant & Gould P.C.

[57] ABSTRACT

The present invention relates to a method and apparatus for determining blood oxygen transport, and to measure lipid levels by correlating these levels with the rate at which oxygen diffuses through the red blood cell membrane.

18 Claims, 3 Drawing Sheets

METHOD AND APPARATUS FOR DETERMINING BLOOD OXYGEN TRANSPORT

BACKGROUND OF THE INVENTION

The relationship between elevated blood lipids, particularly cholesterol (and especially low-density-lipoprotein cholesterol) and atherosclerosis has been known for many years. More recently, reduction of LDL cholesterol by means of surgery or drugs has been shown to reduce the risk of coronary heart disease. However, the reduction of cardiac events achieved by cholesterol lowering does not correlate well with the relatively small amount of physical regression in the amount of atherosclerotic plaque seen in the coronary arteries following treatment. In addition, relief of angina pectoris (ischemic chest pain) often occurs in a matter of weeks following cholesterol lowering; whereas, documentable changes in the inside diameters of coronary arteries may take years to occur, if they occur at all. The pain associated with angina pectoris is attributable primarily to lactic acid produced when heart muscle cell metabolism occurs in the absence of oxygen. Coronary artery narrowing can limit the amount of blood-transported oxygen that reaches the heart muscle tissue, but, the above observation suggests oxygenation of heart muscle tissue can be improved without increasing blood flow through the coronary vessels.

The way in which changes in blood lipids, such as cholesterol, might affect oxygen delivery to heart muscle tissue has remained unclear. There is abundant oxygen in blood. In fact, oxygenated (arterial) blood contains approximately as many molecules of oxygen per 1000 mL as are found in 200 mL of oxygen gas. Almost all (98–99%) of this oxygen is bound to hemoglobin molecules within the red blood cells; the remainder is physically dissolved in plasma and intracellular red blood cell fluid. For oxygen to reach tissues, such as cardiac muscle tissue, oxygen must be released from hemoglobin and then diffuse across the red blood cell membrane into the plasma and from there into tissues. The movement of oxygen across the red blood cell membrane occurs by passive diffusion and is governed by concentration gradients; there is no active membrane transport system for oxygen. Furthermore, the composition of a subject's red blood cell membrane changes with changes in the subject's lipid status. Therefore, the red blood cell membrane can be a significant barrier to release of oxygen into tissue such as cardiac muscle tissue.

What is needed is a method and apparatus to assess the significance of the red blood cell membrane as a hindrance to oxygen transfer from blood to tissues, such as cardiac muscle tissue. Such a method and apparatus would provide a new way to assess heart and circulatory disorders related to oxygen transport, such as angina pectoris; a new way to measure, and to assess the impact of, a patient's blood lipid levels; and a new way to monitor the effectiveness of lipid-lowering therapies.

SUMMARY OF THE INVENTION

The present invention relates to an apparatus and method for determining the rate at which oxygen crosses the red blood cell membrane. The apparatus and method provide a way to assess heart and circulatory disorders related to oxygen transport. Advantageously, the apparatus and method of the invention can be used to assess a patient's susceptibility to angina pectoris, to determine a patient's blood lipid levels, and to follow the course of a lipid-lowering therapy.

The present method of determining a patient's blood lipid level, and its impact, includes measuring rates of oxygen diffusion across red blood cell membranes from the patient. This rate(s) indicates the blood lipid level, for example, through correlating a measured rate with a previously determined rate(s) for an established level(s) of blood lipid. Advantageously, red blood cell samples are standardized to generally uniform conditions of gas content by exposing the red blood cell to oxygen and exposing the red blood cell to an environment depleted of oxygen as part of the measurement process. Preferably, the rate at which oxygen moves across the red blood cell membrane is determined by monitoring either a blood plasma level of oxygen, a level of oxygen bound to hemoglobin, or both.

In one embodiment, the method of the invention can be used to assess a patient's susceptibility to angina pectoris. This embodiment includes measuring a rate of oxygen diffusion across a membrane of a red blood cell from the patient. This rate indicates the patient's susceptibility to angina pectoris, for example, by correlating the measured rate with the susceptibility to angina observed in a control or standardized population, or in the patient, at the measured rate.

In another embodiment, the method of the invention can be used to follow the course of a lipid-lowering therapy. This embodiment includes measuring a rate of oxygen diffusion across a membrane of a red blood cell from the patient. This rate determines the effectiveness of a lipid-lowering therapy, for example, by correlating the measured rate with lipid levels to determine the patient's relative or absolute lipid level, and comparing the patients lipid level to the patient's previous lipid levels.

The apparatus of the invention, which is suitable for conducting the methods of the invention, measures diffusion of oxygen across a red blood cell membrane and includes an oxygen level detector, a gas exchange system, and a red blood cell transport system. The red blood cell transport system is adapted and configured for transporting red blood cells through the gas exchange system and the oxygen level detector. The gas exchange system is adapted and configured to exchange gasses with the red blood cell. The oxygen level detector is adapted and configured for detecting oxygen levels in a red blood cell or in fluid (e.g., plasma) surrounding a red blood cell.

In a preferred embodiment of the apparatus, the oxygen level detector is a spectrophotometric detector, the red blood cell transport system is a pump, and the gas exchange system is a closed loop diffusion system. The preferred closed loop diffusion system includes gas permeable tubing in a chamber defined by a housing. The gas permeable tubing has a lumen effective for containing red blood cells and for diffusion of gas through the tubing and to and the red blood cells. The housing is adapted and configured for containing successive samples of gases to effect gas exchange with the red blood cells.

DETAILED DESCRIPTION OF THE INVENTION

Figure 1:
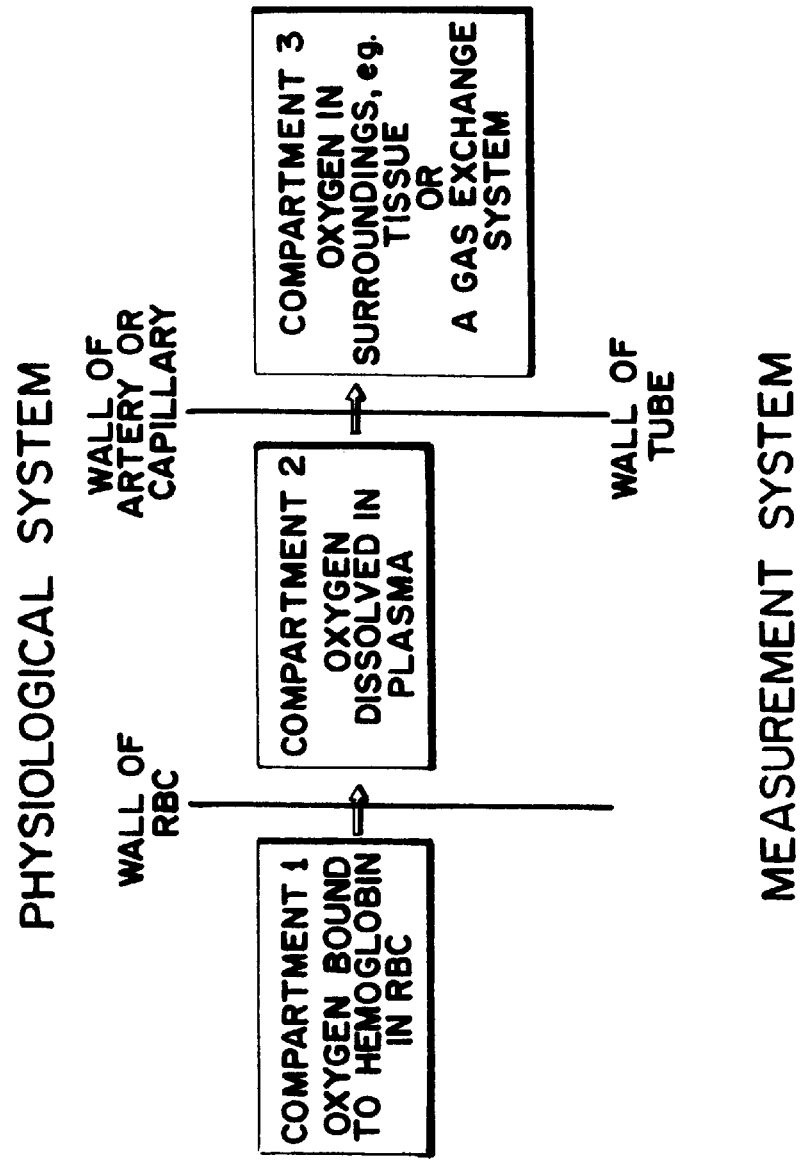
FIG. 1 illustrates three compartments associated with the circulation of blood, involved in oxygen transfer and utilization, and that can be modeled in an apparatus for measuring oxygen levels.

The present invention relates to a method and apparatus for measuring the rate of oxygen diffusion across a red blood cell membrane. The method and apparatus can be employed to monitor treatment of or to diagnose disorders of blood, heart, and/or circulation, such as angina pectoris. The method and apparatus can also be employed for determining a patient's blood lipid level.

Oxygen Diffusion Through Red Blood Cell Membranes
Measuring Oxygen Levels

Oxygen levels in gasses, in liquids, in blood, such as in blood cells or plasma, and in tissues can be measured in several ways and using a variety of instruments that are known in the art. An oxygen electrode detects free molecular oxygen in a liquid and can be used with biological fluids such as blood, plasma, and the like. Oxygen can also be detected by known spectrophotometric methods, either free or as part of a complex with another molecule.

In red blood cells, nearly all oxygen present is complexed with hemoglobin. Such complexes can be detected by numerous methods known in the art, including spectrophotometric methods, fluorometric methods, potentiometric methods, and the like. For example, for absorption of light in the uv/visible range, the greatest difference in absorbance between hemoglobin and oxygenated hemoglobin occurs at 660 nm. At 805 nm, the isobestic point, there is no difference in absorbance between oxygenated hemoglobin and hemoglobin. Typically, scattering of light by blood components is accounted for by determining absorbance at a wavelength where neither hemoglobin nor oxygenated hemoglobin significantly absorb light. After accounting for scattering, the difference in absorbance at 660 nm yields the concentration of oxygenated hemoglobin. Various instruments exist for convenient and automated measurements of levels of oxygenated hemoglobin.

A small amount of the oxygen present in blood is not complexed with hemoglobin, and can be detected as oxygen in plasma. Plasma oxygen can be detected by numerous methods known in the art, including spectrophotometric methods, fluorometric methods, potentiometric methods, and the like. For example, excitation of a plasma sample at 385 nm results in fluorescence of plasma oxygen which is detectable at 515 nm. Light scattering can be taken into account by a measurement at a wavelength outside the range of fluorescence of absorption of oxygen in plasma. Various instruments exist for convenient and automated measurements of levels of plasma oxygen.

Employing one or more instruments that can determine oxygenated hemoglobin and determine plasma oxygen in a system allows both forms of oxygen to be determined in a single sample. Advantageously, in the method and apparatus of the invention a single instrument or detector can determine both oxygenated hemoglobin and plasma oxygen. Measurement of one or both of the plasma oxygen level and/or the level of oxygenated hemoglobin determines a rate at which oxygen crosses the red blood cell membrane to move from being oxygenated hemoglobin to being plasma oxygen. Either or both of these levels can be monitored continuously or intermittently. Alternatively, measuring an amount or level after a predetermined time period can also yield a rate of diffusion across the red blood cell membrane.

Oxygen in Blood, Tissues, and Model Systems

FIG. 1 shows three compartments associated with circulation of blood, that are involved in oxygen transfer and utilization, and that can be modeled in an apparatus for measuring oxygen levels. Oxygen levels can be measured in any or all of these compartments.

Compartment one represents the interior of a red blood cell. A red blood cell lacks a nucleus, organelles, and any internal membranous structures. The cell membrane is the only membrane of a red blood cell; the red blood cell is basically a membranous sack containing hemoglobin. Oxygen in a red blood cell faces only two barriers to exiting the cell, dissociating from hemoglobin and diffusing across the red blood cell membrane. Dissociation from hemoglobin is fast compared to diffusion across the red blood cell membrane. Therefore, the rate at which oxygen leaves a red blood cell reflects the rate at which oxygen diffuses through or across the red blood cell membrane.

The level of oxygen in compartment one is the level of oxygenated hemoglobin in the red blood cell. Only negligible oxygen in a red blood cell is free of hemoglobin. In a red blood cell total oxygen content can be measured by any of several known methods. For example, by the amount of hemoglobin and the level of oxygen saturation ($S_{O2}$) of the hemoglobin. The level of oxygen saturation is defined by the concentration of oxygenated hemoglobin [HbO] divided by the concentration of total hemoglobin [Hb] times 100%; [HbO]/[Hb]×100%. This can be measured by a variety of methods and instruments known in the art.

Compartment two represents the blood outside of the red blood cell and can include other blood cells, proteins, plasma, serum components, laboratory additives (e.g. anticoagulants), and the like. Compartment two generally contains only a small amount of the total oxygen in blood. However, any oxygen entering or leaving the blood must cross through this compartment on its way to hemoglobin, the oxygen transport vehicle. Therefore, the level of oxygen in compartment two reflects the flux of oxygen from compartment one to compartment three, and also in the reverse direction. Oxygen levels in compartments one and three will affect the oxygen level in and the rate of change of oxygen level in compartment two.

The level of oxygen in compartment two can be represented by plasma oxygen levels. This can be measured as $P_{O2}$, the partial pressure of oxygen in plasma. This measurement can be conducted by a variety of methods and instruments known in the art. Since partial pressure measurements are affected only by gas molecules free in solution, oxygen that is bound to hemoglobin is not included in instantaneous $P_{O2}$ measurements. Over time, however, the hemoglobin does affect $P_{O2}$ values by acting as an oxygen sink which removes excess oxygen from the plasma when levels are high and replaces plasma oxygen when levels are low.

Compartment three represents the surroundings of a vessel or tube carrying blood. In an animal, compartment three represents tissue that surrounds a blood vessel. Lung tissue supplies oxygen to the blood via diffusion of oxygen through the blood vessel wall and across the membrane of the red blood cell, leading to the formation of oxygenated hemoglobin. Other tissues are nourished by oxygen that dissociates from hemoglobin, crosses the red blood cell membrane, leaves the blood vessel, and enters the tissue. In an apparatus that measures oxygen levels in blood or blood components, compartment three typically represents the surroundings of a tube, such as a gas permeable silicon or silastic tube, carrying blood. In such an apparatus, compartment three can be a gas or liquid (fluid) filled container from which oxygen can diffuse through the tube and into compartments two and one. In addition, in such an apparatus, oxygen can diffuse from compartments one and two into compartment three.

In the method and apparatus of the present invention, the oxygen concentration in compartment three can be controlled. This allows control of the direction and amount of flow of oxygen into and out of compartments one and two. In the method and apparatus of the invention, measuring the amount of oxygen in either or both of compartments one and two reveals the direction and rate of movement of oxygen. For example, depletion of oxygen in compartment three will deplete oxygen in the plasma, and oxygen will dissociate from oxygenated hemoglobin, diffuse through the membrane of the red blood cell and out of the cell. When the concentration of oxygen in compartment three is higher than the concentration in compartment two, the plasma will become oxygenated, and oxygen will diffuse through the membrane of the red blood cell and into the cell, and form oxygenated hemoglobin.

Measuring Oxygen Diffusion Across a Red Blood Cell Membrane

The lipid content, particularly the cholesterol content, of the red blood cell membrane affects the diffusion of oxygen through the red blood cell membrane. The cholesterol content of the red blood cell membrane in turn reflects blood cholesterol levels. Therefore, the rate at which oxygen crosses the red blood cell membrane provides a measure of blood cholesterol levels and is useful in diagnosis and treatment of coronary artery disease and other heart and circulatory disorders. The present invention includes a method for measuring the rate at which oxygen diffuses across the red blood cell membrane, which includes embodiments directed to methods of evaluating lipid-lowering treatments, methods of diagnosing or assessing the risk of heart and circulatory disorders such as angina pectoris, and methods of determining a patient's blood lipid level.

The present method of determining a patient's blood lipid level typically includes the steps of obtaining a blood sample from a patient, measuring a rate of oxygen diffusion across a membrane of a red blood cell, and, preferably, correlating the measured rate with established levels of blood lipid to determine the patient's blood lipid level.

The step of measuring the rate of oxygen diffusion across a membrane of a red blood cell, preferably, includes the steps of exposing the red blood cell to oxygen; exposing the red blood cell to an environment depleted of oxygen; and monitoring either a blood or plasma level of oxygen, a level of oxygen bound to hemoglobin, or both. A blood sample obtained from a patient or subject can contain varying amounts of oxygen, and the rate at which oxygen crosses the red blood cell membrane can, in certain conditions, depend on the amount of oxygen present. Exchanging gasses, either by exposing the red blood cells to oxygen or by exposing the red blood cell to an environment depleted of oxygen, standardizes the blood sample to a predetermined level of oxygen and allows significant comparison of numerous blood samples. The red blood cell can be first exposed to oxygen and subsequently exposed to an environment depleted of oxygen. When exposure to oxygen precedes depletion, oxygen is released from red blood cells during and after depletion, and monitoring, typically, monitors this release. Alternatively, the red blood cell can be first exposed to an environment depleted of oxygen and subsequently exposed to oxygen. When depletion of oxygen precedes exposure to oxygen, oxygen is taken up by the red blood cells during exposure, and monitoring, typically, monitors this uptake.

In a preferred embodiment, exposing the red blood cell to oxygen includes circulating a blood sample in a closed loop diffusion system 17. Typically the closed loop diffusion system 17 includes a chamber 13 containing an atmosphere including oxygen. The level of oxygen in chamber 13 can vary over a wide range. The red blood cells can be exposed to any concentration suitable for standardizing the oxygen level between no oxygen and 100% oxygen. Preferably, the partial pressure of oxygen in chamber 13 is about oxygen's partial pressure in air. That is, the atmosphere in chamber 13 includes oxygen at atmospheric gas pressure, for example, 160 mm Hg $O_2$ with 4 mm Hg $CO_2$. Alternatively, the partial pressure of oxygen in chamber 13 can be about oxygen's partial pressure in a capillary. That is, the atmosphere in chamber 13 includes oxygen at pressure, for example, of about 23 mm Hg $O_2$ with 46 mm Hg $CO_2$. Preferably the blood reaches equilibrium with oxygen or with both oxygen and carbon dioxide. Typically this step of circulating lasts for about 6 min.

In a preferred embodiment, exposing the red blood cell to an environment depleted of oxygen includes circulating a blood sample in closed loop diffusion system 17, with closed loop diffusion system 17 including chamber 13 containing an atmosphere depleted of oxygen. For example, a suitable oxygen depleted atmosphere is nitrogen or another inert gas, preferably nitrogen. Typically, a commercial or medical grade of nitrogen gas can be employed. Preferably, this depleting step results in complete or nearly complete removal of oxygen from chamber 13, gas permeable tubing 15, and the fluid containing the red blood cells (e.g. plasma). Although considerable deoxygenation is typically observed in the first about 30 seconds, typically, this circulating step lasts longer, preferably, about 15 min.

Monitoring either a blood level of oxygen, a level of oxygen bound to hemoglobin, or both can be accomplished employing a variety of methods or instruments, as described herein. Monitoring can take place continuously or intermittently through the exposing and circulating steps, or only at two or more discrete time points. For example, the method can include the step of determining the level of saturation of hemoglobin with oxygen achieved during the step of exposing the red blood cell to oxygen.

In one embodiment, measuring the rate of oxygen diffusion across a red blood cell membrane includes monitoring the ratio of $S_{O2}/P_{O2}$ and plotting this ratio as a function of time under the following conditions:

a) The blood sample is oxygenated, preferably to its maximum, by subjecting compartment three to 1–100% oxygen. Then, $S_{O2}/P_{O2}$, $S_{O2}$, and/or $P_{O2}$ can be measured.

b) The blood sample is subjected to a 0% oxygen environment (e.g., 100% nitrogen or another inert gas) in compartment three. Then, $S_{O2}/P_{O2}$, $S_{O2}$, and/or $P_{O2}$ can be measured, preferably continually, over time.

In these conditions, free oxygen has been depleted, but oxygenated hemoglobin remains a source of oxygen. Release of oxygen from oxygenated hemoglobin, which decreases the level of oxygenated hemoglobin, supplies oxygen to the plasma by diffusion through the red blood cell membrane. To the extent that this diffusion is slowed by the membrane, the plasma levels of oxygen ($P_{O2}$) remain depressed for a longer period. Therefore, the rate at which plasma oxygen levels increase provides a measure of the rate of diffusion of oxygen through the red blood cell membrane.

Figure 2:
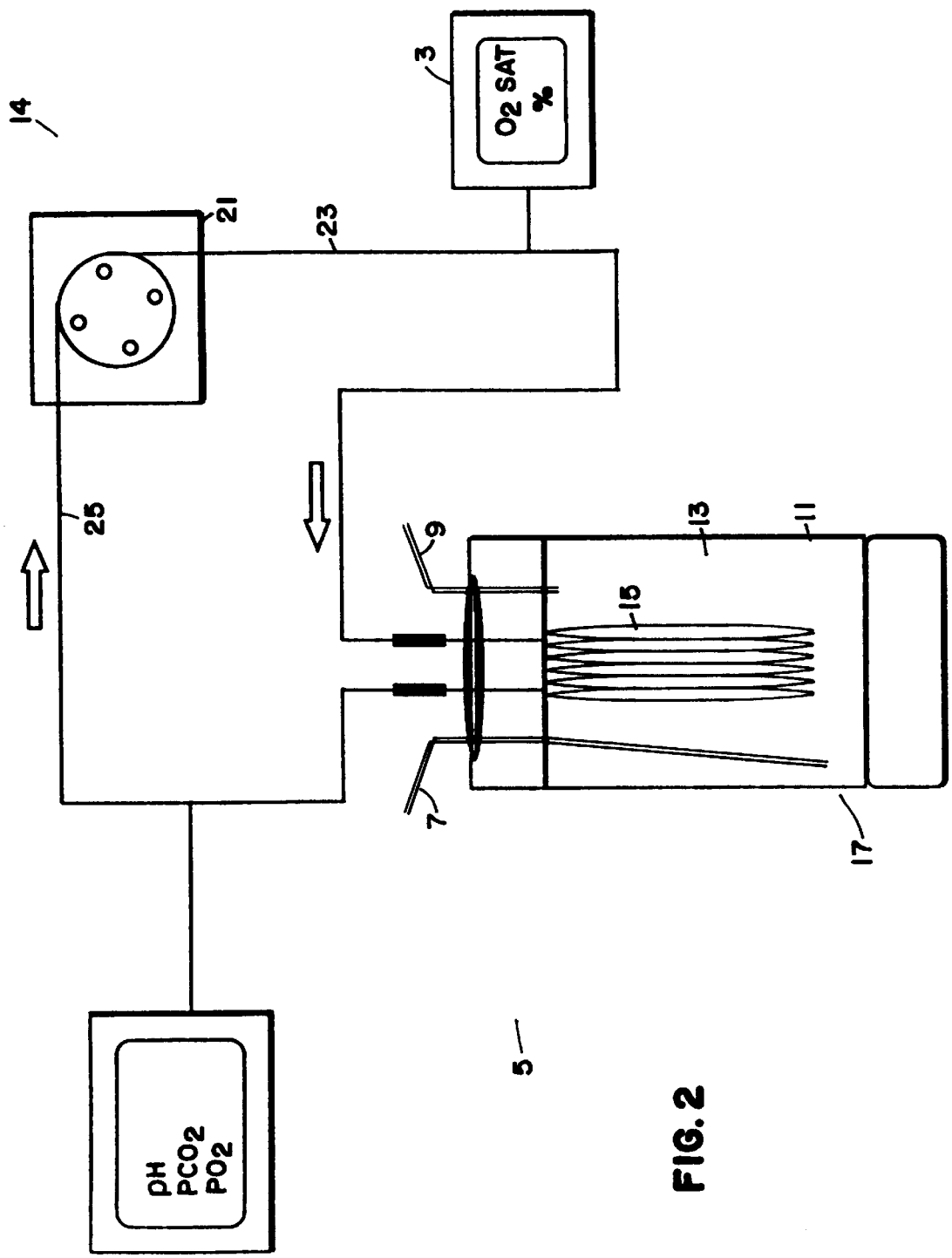
FIG. 2 illustrates an embodiment of the apparatus of the invention.

Apparatus for Measuring the Rate of Oxygen Diffusion Across a Red Blood Cell Membrane FIG. 2 illustrates an apparatus for measuring the rate of oxygen diffusion across a red blood cell membrane. The apparatus includes an oxygen level detector, a gas exchange system, and a red blood cell transport system. The red blood cell transport system is adapted and configured for transporting red blood cells through the gas exchange system and the oxygen level detector. The gas exchange system is adapted and configured to exchange gasses with the red blood cell. The oxygen level detector is adapted and configured for detecting oxygen levels in a red blood cell or in fluid surrounding a red blood cell.

Oxygen level detector 3 can be any of several detectors suitable for detecting oxygen levels in plasma or anther fluid and/or for detecting oxygenated hemoglobin or another oxygen complex. For example, oxygen detector 3 can include an oxygen electrode, a spectrophotometric detector, a fluorometric detector, or a combination of such electrodes and/or detectors. Preferably, oxygen level detector 3 includes detectors for spectrophotometric determination of both plasma oxygen and oxygenated hemoglobin. Preferably, oxygen level detector 3 is a dual or multiple wavelength spectrophotometer. Oxygen level detector 3 can be any of a variety of known or commercially available oxygen level detectors.

Preferably, oxygen level detector 3 includes: a light source capable of producing light of 385 nm, 660 nm, 805 nm and an absorption free wavelength; one or more filters to sequentially submit a blood sample to these wavelengths; a cell to allow blood to flow slowly through this light system; and photopickups to detect the transmission of light through the sample at each wavelength. Preferably oxygen level detector 3 is coupled to appropriate electronics and microprocessors to derive the amounts of, or changes in amounts of, plasma oxygen and oxygenated hemoglobin from the comparative signals.

Gas exchange system 5 typically includes a source of gas (not shown), a gas inlet 7, a gas outlet 9, a housing 11 that defines a chamber 13, and a gas permeable tubing 15. These components are typically assembled as a closed loop diffusion system 17. Gas permeable tubing 15 has a lumen (not shown) that is used to contain, preferably flowing, fluid containing red blood cells. A preferred fluid containing red blood cells is blood that has been treated with an anticoagulant. Gas permeable tubing 15 is constructed to allow diffusion of gasses from chamber 13 into the lumen and into any fluid in the lumen and is preferably made of silicone or silastic material. Gas is introduced into chamber 13 through gas inlet 7, and exits through gas outlet 9. Preferably, gas flows through chamber 13 to remove any gas that diffuses from gas permeable tubing 15 and to replace any gas the diffuses into gas permeable tubing 15. Housing 11 can be a stoppered laboratory flask, such as an Erlenmeyer flask. Gas exchange system 5 can be any of several suitable system for exchanging gas into red blood cells, blood, or another fluid.

Red blood cell transport system 19 typically includes a pump 21, inflow tubing 23, and outflow tubing 25. Red blood cell transport system 19 transports plasma or another fluid containing red blood cells through one or more oxygen level detectors 3, into gas exchange system 5, and from gas exchange system 5 back to pump 21. Preferably, pump 21 is a peristaltic pump. Alternatively, red blood cell transport system can include an aspirator, an apparatus that causes flow based on capillary action, or any of several other suitable apparatus for transporting fluids containing red blood cells. Typically red blood cell transport system 19 includes components necessary for monitoring and recording flow rate and like characteristics as a function of time.

Oxygen Diffusion, Cholesterol Levels, and Angina

The rate (or amount in a unit of time) of oxygen diffusion through a red blood cell membrane has been shown to correlate with blood lipid, particularly cholesterol, levels in the membrane and in plasma. This makes the rate of oxygen diffusion though red blood cell membranes useful in treatment and diagnostic regimes for numerous heart or circulatory disorders. Since the present method and apparatus require only a blood sample, they offer an alternative to existing methods, such as arteriography, that is noninvasive and less expensive. In addition, the present device and method allow earlier monitoring of therapy than waiting for an effect on a parameter such as the diameter of a coronary artery.

Treatment of several heart and circulatory disorders involves therapy, such as administration of medicines, directed at lowering a patient's blood lipid levels. Current methods of following the cardiovascular progress of lipid-lowering therapies are expensive and time-consuming. In one embodiment, the method of the invention can be used to follow the course of such lipid-lowering therapy. This embodiment includes measuring a rate of oxygen diffusion across a membrane of a red blood cell from the patient. This rate determines the effectiveness of a lipid-lowering therapy, for example, by correlating the measured rate with lipid levels to determine the patient's relative or absolute lipid level, and comparing the patient's lipid level to the patient's previous lipid levels.

Certain heart and circulatory disorders, such as angina pectoris, have a frequency and severity that correlate with blood levels of cholesterol and like lipids. In one embodiment, the method of the invention can be used to assess a patient's susceptibility to angina pectoris. This embodiment includes measuring a rate of oxygen diffusion across a membrane of a red blood cell from the patient. This rate indicates the patient's susceptibility to angina pectoris, for example, by correlating the measured rate with the susceptibility to angina observed in a control population, or in the patient, at the measured rate.

The present invention may be better understood with reference to the following examples. These examples are intended to be representative of specific embodiments of the invention, and are not intended as limiting the scope of the invention.

EXAMPLES

Example 1

Correlation of Cholesterol Levels With Red Blood Cell Oxygen Diffusion in an Animal Model This study determined a correlation between the level of a blood lipid, cholesterol, and the rate at which oxygen diffused out of red blood cells.

Materials and Methods

Ten New Zealand White Rabbits were divided into an experimental group and a control group. The six experimental rabbits were fed for eight weeks a diet of standard laboratory rabbit chow supplemented with 0.25% cholesterol. The four control rabbits received, for the same period, the same diet lacking the added cholesterol. After eight weeks on this diet, blood samples were collected from each rabbit by standard methods using sodium heparin as an anticoagulant. The plasma and red blood cell cholesterol levels were determined in an aliquot of each blood sample by the Allain's assay, a standard method.

Another aliquot of each blood sample was circulated through a closed loop diffusion chamber in gas permeable tubing and exposed to atmospheric pressures of oxygen (160 mm Hg) and carbon dioxide (4 mm Hg) for 6 min. (time 6–12 minutes in FIG. 3). This was considered full saturation of the blood with oxygen. Each blood sample was then subjected to desaturation by circulating the blood sample through the closed loop diffusion chamber and exposing the sample to nitrogen gas for 15 minutes (time 12–27 minutes in FIG. 3). During exposure to oxygen and during exposure to nitrogen, each sample was subjected to continuous blood gas monitoring for pH, $P_{CO2}$, and $P_{O2}$.

Results

Figure 3:
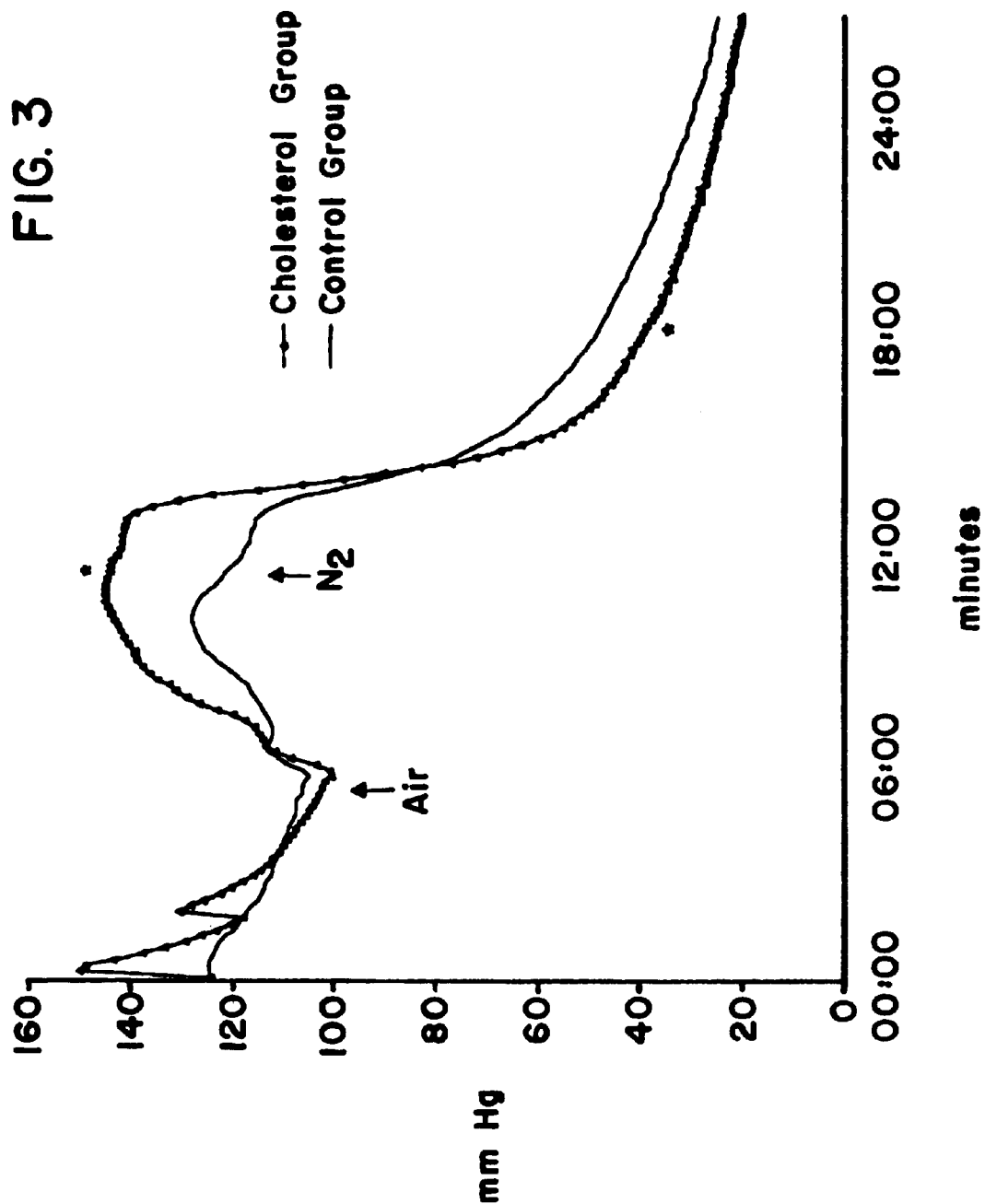
FIG. 3 illustrates the plasma oxygen levels for cholesterol-fed and control animals as determined by an embodiment of the method of the invention.

The results of this study are shown in Table 1 and FIG. 3. Table 1 illustrates that the experimental, cholesterol-fed animals had higher levels of cholesterol both in their plasma and in their red blood cell membranes than the control animals.

This higher level of cholesterol in plasma and in red blood cell membranes correlated with slower diffusion of oxygen through the red blood cell membrane (FIG. 3). FIG. 3 shows that the cholesterol-fed animals achieved higher levels of plasma oxygen during the saturation phase due to slower uptake by the red blood cells. When the cells were exposed to the nitrogen atmosphere, oxygen was exchanged out of the cholesterol-fed rabbit plasma more quickly than the control rabbit plasma. This indicates that red blood cell oxygen diffused more slowly into the plasma from the red blood cells from the cholesterol-fed rabbits than in the control blood.

TABLE 1

Cholesterol levels in rabbit plasma and red blood cell membranes in control and experimental groups after eight weeks of feeding.

| | Cholesterol (mg/dl) | | | |
|---|---|---|---|---|
| | Plasma | | Red Blood Cell Membrane | |
| Group | Mean | SEM | Mean | SEM |
| Control | 60 ± | 1.2 | 22 ± | 1.7 |
| Cholesterol | 928 ± | 31* | 121 ± | 3* |

*p < 0.05 vs. Control Group

Conclusion

Oxygen diffused more slowly across the red blood cell membranes of animals with the higher level of cholesterol in plasma or in red blood cell membrane. This indicates that the rate of diffusion of oxygen across a red blood cell membrane correlates with increased levels of the blood lipid cholesterol in an animal model commonly used in this field for study of blood lipids.

Example 2

Correlation of Cholesterol Levels With Red Blood Cell Oxygen Diffusion in Humans This study determined a correlation between the level of a blood lipid, cholesterol, and the amount of oxygen that diffused into human red blood cells in 15 minutes.

Materials and Methods

Blood samples were collected by standard methods from four informed human volunteers with varying cholesterol levels. Cholesterol levels were determined in one aliquot of each blood sample by Abell's assay, a standard method. Another four aliquots from each blood sample were subjected to blood gas analysis as follows: Each aliquot was subjected to desaturation as described in Example 1 and the amount of oxygen bound to hemoglobin (Hb) was determined. Then, the aliquot was circulated through a diffusion chamber and exposed to capillary gas pressures, 23 mm Hg of $O_2$ and 46 mm Hg $CO_2$. After 15 minutes of circulation, the amount of oxygen bound to hemoglobin (Hb) was determined again.

Results

The results of this study are presented in Table 2. The results presented in Table 2 show that the amount of oxygen that crossed the red blood cell membrane decreased as the cholesterol level increased.

TABLE 2

Correlation with cholesterol levels of amounts of oxygen bound to hemoglobin in human red blood cells before and after exposure to oxygen.

| | | $O_2$ Content (ml/gm of Hb) | | | | | |
|---|---|---|---|---|---|---|---|
| | P Chol | Pre-Diffusion | | Post-Diffusion | | % | p |
| Sample | (mg/dl) | Mean | SEM | Mean | SEM | Change | Value |
| A | 87 | 13.3 ± | 0.391 | 20.5 ± | 0.478 | 35% | 0.037 |
| B | 157 | 14.8 ± | 0.091 | 19.5 ± | 0.270 | 24% | 0.041 |
| C | 241 | 15.8 ± | 0.013 | 20.2 ± | 0.551 | 22% | 0.020 |
| D | 400 | 16.3 ± | 0.079 | 17.5 ± | 0.196 | 7% | 0.014 |

Conclusion

Oxygen diffused more quickly across the red blood cell membranes of humans with the lower level of cholesterol. This indicates that the rate of diffusion of oxygen across a red blood cell membrane correlates inversely with increasing levels of the blood lipid cholesterol in humans.

The invention has been described with reference to various specific and preferred embodiments and techniques. However, it should be understood that many variations and modifications may be made while remaining within the spirit and scope of the invention.

What is claimed is:

1. A method for determining a patient's blood oxygen transport and lipid level, comprising the steps of:
   obtaining a blood sample from the patient;
   measuring a rate of oxygen diffusion across a membrane of a red blood cell of the blood sample; and
   correlating the measured rate with established levels of blood lipid to determine the patient's blood lipid level.

2. The method of claim 1, wherein the step of measuring comprises:
   exposing the red blood cell to oxygen;
   exposing the red blood cell to an environment depleted of oxygen; and
   monitoring either a plasma oxygen level, a level of oxygen bound to hemoglobin, or both.

3. The method of claim 2, wherein exposing the red blood cell to an environment depleted of oxygen comprises circulating a blood sample in a closed loop diffusion chamber, the chamber housing an atmosphere comprising nitrogen and depleted of oxygen.

4. The method of claim 3, wherein the atmosphere is supplied from a container of commercial grade nitrogen gas.

5. The method of claim 3, wherein circulating lasts for about 15 min.

6. The method of claim 2, wherein the step of exposing the red blood cell to oxygen precedes the step of exposing the red blood cell to an environment depleted of oxygen.

7. The method of claim 2, wherein the step of exposing the red blood cell to an environment depleted of oxygen precedes the step of exposing the red blood cell to oxygen.

8. The method of claim 2, wherein exposing the red blood cell to oxygen comprises circulating a blood sample in a closed loop diffusion chamber, the chamber housing an atmosphere comprising oxygen.

9. The method of claim 8, wherein the atmosphere comprising oxygen comprises capillary gas pressures.

10. The method of claim 9, wherein the gas pressures comprise about 23 mm Hg $O_2$ and about 46 mm Hg $CO_2$.

11. The method of claim 8, wherein circulating lasts for about 6 min.

12. The method of claim 8, wherein the atmosphere comprising oxygen comprises atmospheric gas pressures.

13. The method of claim 12, wherein the gas pressures comprise about 160 mm Hg $O_2$ and about 4 mm Hg $CO_2$.

14. The method of claim 1, wherein the measuring step is performed on a whole blood sample comprising anticoagulant.

15. A method for determining a patient's susceptibility to angina, comprising the steps of:

obtaining a blood sample from the patient;

measuring a rate of oxygen diffusion across a membrane of a red blood cell of the blood sample; and correlating the measured rate with the susceptibility to angina observed in a control population, or in the patient, at the measured rate.

16. The method of claim 15, wherein the step of measuring comprises:

exposing the red blood cell to oxygen;

exposing the red blood cell to an environment depleted of oxygen; and monitoring either a plasma oxygen level, a level of oxygen bound to hemoglobin, or both.

17. A method for determining the effectiveness of a lipid-lowering therapy, comprising the steps of:

obtaining a blood sample from a patient undergoing a lipid-lowering therapy;

measuring a rate of oxygen diffusion across a membrane of a red blood cell of the blood sample;

correlating the measured rate with established levels of blood lipid to determine the patient's relative or absolute blood lipid level; and comparing the patient's lipid level to the patient's previous lipid level measured at an earlier time in order to determine if the lipid level of the patient has been lowered by the lipid-lowering therapy.

18. The method of claim 17, wherein the step of measuring comprises:

exposing the red blood cell to oxygen;

exposing the red blood cell to an environment depleted of oxygen; and monitoring either a plasma oxygen level, a level of oxygen bound to hemoglobin, or both.

* * * * *